United States Patent [19]
Mittelmeier et al.

[11] Patent Number: 5,788,703
[45] Date of Patent: Aug. 4, 1998

[54] APPARATUS FOR THE PLACEMENT OF A MEDULLARY SPACE BLOCKER

[75] Inventors: Wolfram Mittelmeier, Lübeck; Urs Limacher, Hünenberg, both of Germany

[73] Assignee: Allo Pro AG, Baar, Switzerland

[21] Appl. No.: 582,059

[22] Filed: Jan. 2, 1996

[30] Foreign Application Priority Data

Feb. 17, 1995 [EP] European Pat. Off. ............. 95810107

[51] Int. Cl.$^6$ ........................................ A61B 17/56
[52] U.S. Cl. .................................... 606/94; 606/95
[58] Field of Search ...................... 606/94, 93, 92, 606/95, 191–199

[56] References Cited

U.S. PATENT DOCUMENTS

| | | |
|---|---|---|
| 4,399,814 | 8/1983 | Pratt . |
| 4,462,394 | 7/1984 | Jacobs ............................. 606/94 |
| 4,488,549 | 12/1984 | Lee . |
| 4,627,434 | 12/1986 | Murray ............................ 606/94 |
| 4,815,454 | 3/1989 | Dozier ............................. 606/94 |
| 5,078,746 | 1/1992 | Garner ............................. 623/16 |
| 5,147,366 | 9/1992 | Arroyo et al. ................... 606/94 |
| 5,468,245 | 11/1995 | Vargas, III ...................... 606/94 |

FOREIGN PATENT DOCUMENTS

| | | |
|---|---|---|
| 0093560 | 11/1983 | European Pat. Off. . |
| 0178174 | 4/1986 | European Pat. Off. . |
| 8804188 | 10/1989 | France . |
| 2708192 | 2/1995 | France . |
| 2311521 | 9/1973 | German Dem. Rep. . |
| 3835853 A1 | 4/1990 | German Dem. Rep. . |
| 39 37786 A1 | 7/1990 | German Dem. Rep. . |
| WO 93/08769 | 5/1993 | WIPO . |

*Primary Examiner*—Guy V. Tucker
*Attorney, Agent, or Firm*—Townsend and Townsend and Crew LLP

[57] ABSTRACT

A tubular guide part which is insertable into the medullary space is connected to a source of pressure medium and to a blocking element having the form of a hollow body which can be inflated in the manner of a balloon. The hollow body is inflated via the supply of pressure medium from a basic position situated in the cross-sectional region of the guide part into an expanded position in which the hollow body seals off one portion of the medullary space, which is to be filled with bone cement and is to receive a prosthesis shaft, from a neighboring portion of the medullary space. After insertion of a part of the prosthesis shaft into the bone cement bed, the hollow body can be shrunk into its basic position by the removal of pressure medium and withdrawn from the medullary space together with the guide part. The cavity in the bone cement bed ensuing therefrom is filled up by bone cement expelled during insertion of the remaining portion of the prosthesis shaft. In this manner, a medullary space blocker is provided which can be temporarily installed in the medullary space and then removed before the final curing of the bone cement.

10 Claims, 2 Drawing Sheets

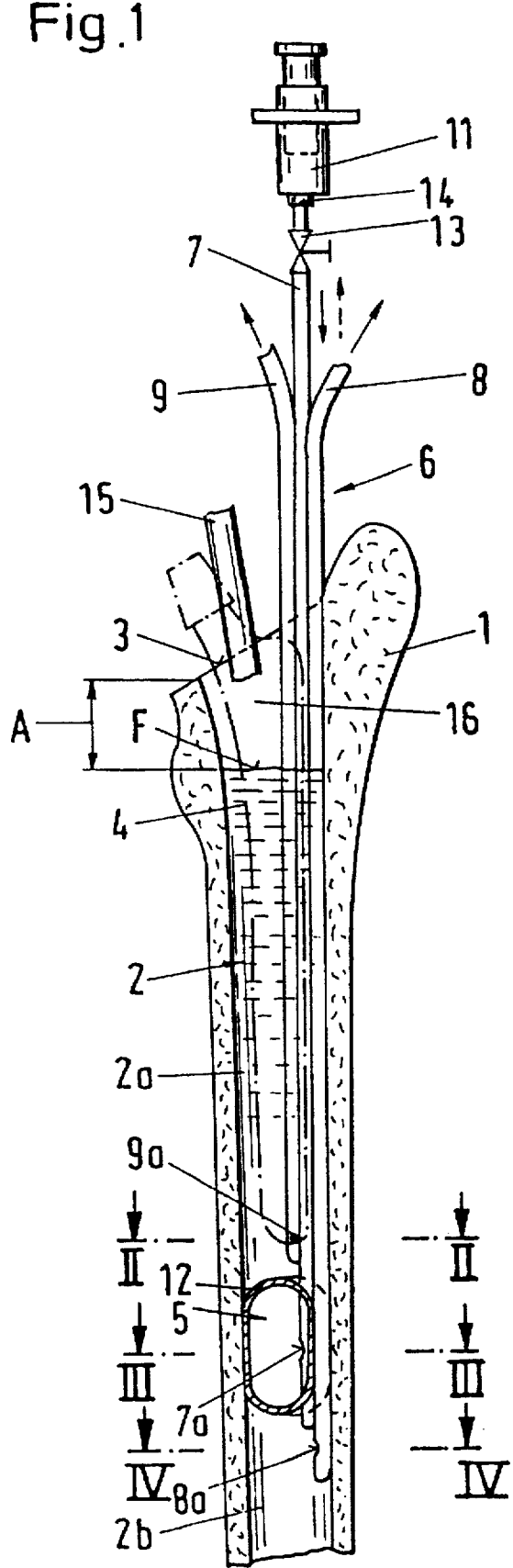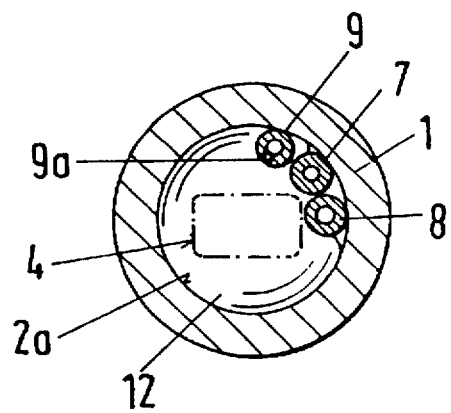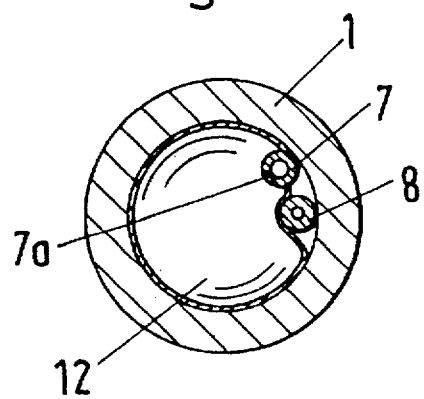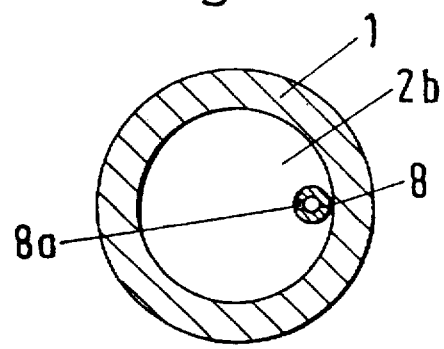

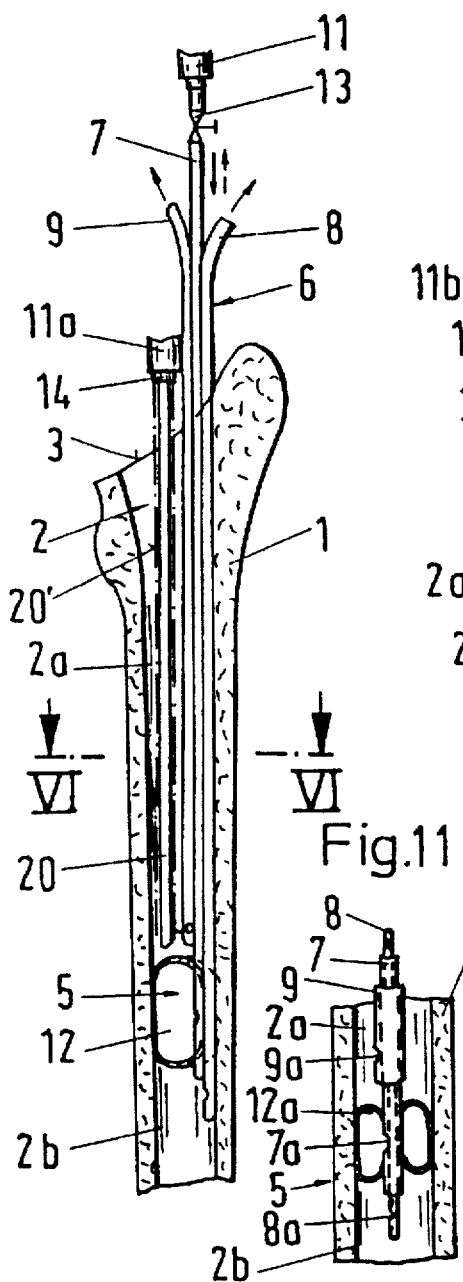
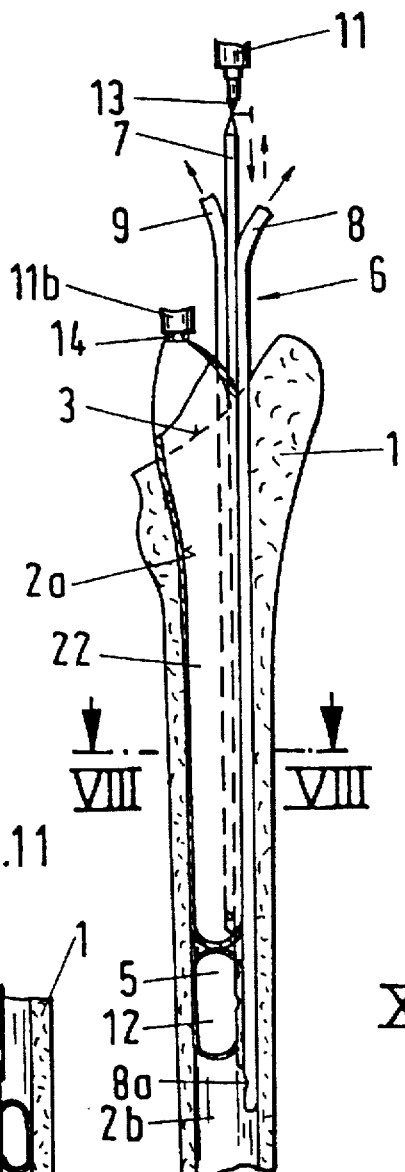
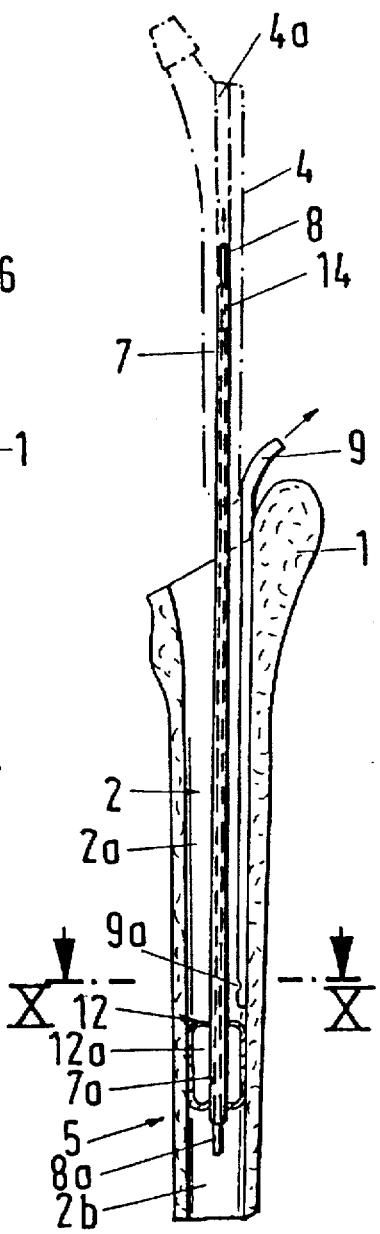
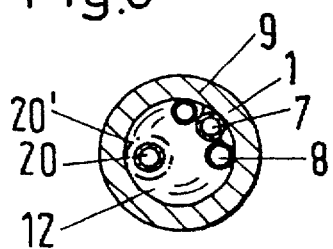
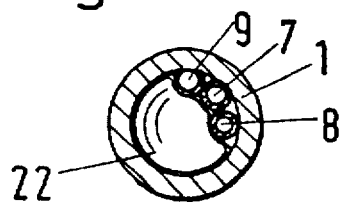
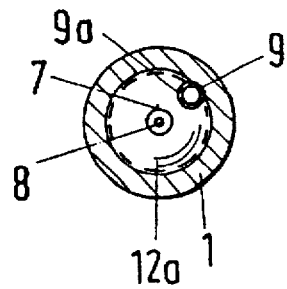

5,788,703

APPARATUS FOR THE PLACEMENT OF A MEDULLARY SPACE BLOCKER

BACKGROUND OF THE INVENTION

1. Field of the Invention

The invention relates to an apparatus for the placement of a medullary space blocker in the medullary space of a tubular bone to be implanted with the use of bone cement.

2. Description of the Prior Art

The invention further relates to a medullary space blocker for a tubular bone of this kind.

Numerous types of medullary space blockers in the form of insertion bodies are known for the inner sealing of an operation cavity into which a prosthesis shaft is to be fitted, which is provided in the medullary space of a tubular bone and which is to be filled with bone cement of the type in which the blocker is anchored in the operation cavity forming a plug remaining in the medullary space to prevent the applied bone cement flowing out of the proximal portion of the medullary space into the distal portion of the medullary space. A known medullary space blocker of the named kind comprises an insertion body which can be inserted into the medullary space with a placement tool and then splayed out. A blocker of this kind can be made of a plastic, for example polyethylene, which is compatible with and durable in the body, or from a metal or metal alloy customary for endoprostheses (EP-A-0 058 744).

Medullary space blockers which remain in the bone have the disadvantage that, in the case of a prosthesis exchange, they have to be removed from the bone. The removal is associated with a certain amount of work which can in some cases be considerable. Furthermore, in medullary space blockers of this kind, problems can occur when the insertion body is insufficiently solidly anchored at for example the application side and/or when the medullary space is insufficiently tightly sealed off. If the anchorage of the insertion part is insufficient, it can slip so that the portion of the medullary space to be filled in with bone cement is extended and thus the sealing of the bone cement is compromised. If the medullary space blocker does not seal to a sufficient degree, the bone cement can pass into the distal portion of the medullary space and/or the pressure pertaining in the distal portion can be increased by air expelled from the proximal portion of the medullary space, which can induce the formation of embolisms.

SUMMARY OF THE INVENTION

The object of the invention is to provide an apparatus of the initially named kind which is improved as well as to provide a correspondingly improved medullary space blocker which can be precisely positioned in the medullary space and achieves a reliable, sealing closure of the medullary space and which makes fewer demands on the tubular bone, in particular in the case of a prosthesis exchange, and which makes it easier to prepare the medullary space during an operation for the receipt of the bone cement.

In accordance with the present invention, apparatus for the placement of a medullary space blocker in the medullary space of a tubular bone intended for the receipt of an anchoring shaft of an endoprosthesis that is to be implanted with the use of bone cement comprises a tubular guide part that can be inserted into and withdrawn from the medullary space. A portion of the tubular guide part that is to be inserted into the medullary space is closed off in an axial direction and is connected to the medullary space blocker.

The medullary space blocker preferably is an elastically deformable blocking element having the form of a hollow body that is expansible in the manner of a balloon. The tubular guide part is connectable outside of the medullary space to a source of a pressure medium, and the hollow body is adjustable between a basic position situated substantially inside the cross-section of the guide part and an expanded position in which the proximal portion of the medullary space to be filled with bone cement is sealed off from a distal portion of the medullary space. The hollow body adopts the basic position when the guide part is relieved of pressure, and the hollow guide body adopts the expanded position upon the supply of a pressure medium.

The apparatus formed in accordance with the invention permits a simple, temporary placement into the medullary space of a blocker element. The blocker element can be sealed against the wall of the medullary space by the supply of a pressure medium, shrunk by the removal of the pressure medium and withdrawn from the medullary space when in this shrunk, basic position. The temporary placement lasts only for a relatively short part of the operation. The blocker element can be returned to its basic position and subsequently withdrawn only a few minutes after applying the bone cement as soon as it displays a predetermined kneedable consistency which the surgeon can ascertain quite straightforwardly. The blocker can be returned to its basic position by letting off the pressure medium. In the basic position, the blocker is situated in the region of the cross-section of the guide part which allows the blocker element to be withdrawn from the partially cured bone cement together with the guide part. The cavity left behind on withdrawal of the guide part can be filled up by compressing the bone cement bed.

BRIEF DESCRIPTION OF THE DRAWINGS

FIG. 1 is an axial partial longitudinal section of a tubular bone having an apparatus for the placement of a medullary space blocker in accordance with the invention;

FIGS. 2, 3 and 4 are cross-sections of the tubular bone corresponding to the lines II—II, III—III and IV—IV of FIG. 1, respectively;

FIGS. 5 and 7 are the tubular bone of FIG. 1 with other apparatuses for the placement of a medullary space blocker in accordance with other embodiments;

FIGS. 6 and 8 are cross-sections of a tubular bone corresponding to the lines VI—VI of FIG. 5 and VIII—VIII of FIG. 7, respectively;

FIG. 9 is the tubular bone of FIG. 1 having an apparatus in accordance with a further embodiment of the invention;

FIG. 10 is a cross-section of the tubular bone corresponding to the line X—X in FIG. 9; and FIG. 11 is a detail of the apparatus shown in FIG. 9 in a modified embodiment.

DETAILED DESCRIPTION OF THE PREFERRED EXEMPLARY EMBODIMENTS

The tubular bone 1 shown in FIG. 1 is a femur. The upper end portion of the femur forms an operation cavity. The operation cavity is provided in the medullary space 2. It is for the receipt of an anchoring shaft 4 of a femur head prosthesis to be placed in an operation aperture 3 and for the receipt of a bone cement bed surrounding the anchoring shaft 4 as well as for the receipt of a medullary space blocker 5. The anchoring shaft 4 is illustrated with the dot-dashed line. The penetration depth of the anchoring shaft 4 is limited by the medullary space blocker 5. The blocker 5 also serves to seal off the proximal portion 2a of the medullary space 2 from the distal portion 2b of the medullary space, wherein the former is to be filled with bone cement.

An apparatus 6 is provided for the placement of the medullary space blocker 5. The apparatus 6 can be inserted into and withdrawn from the medullary space 2 and comprises a tubular guide part 7 and two tubular relief lines 8, 9. The end of the guide part 7 situated outside the medullary space 2 is connectable to a source of pressure medium which, in the diagram, is the pump cylinder of a syringe 11. The syringe 11 can be filled with a pressure fluid, e.g. Ringer's solution. The guide part 7 and the relief lines 8 and 9 can each be formed from a rubber-like material, for example flexible hosing of polyether. The end portions of the guide part 7 and relief lines 8 and 9 which can be inserted into the medullary space 2 can be closed off in the axial direction. The guide part 7 and the relief lines 8 and 9 are each provided with lateral apertures 7a, 8a and 9a, respectively. The ends of the relief lines 8 and 9 protruding out of the medullary space 2 can be open or each connected to a suction device (not shown).

An elastically deformable blocker element in the form of a balloon-like, expansible, thin-walled hollow body 12 is provided as the medullary space blocker 5. The hollow body 12 is made of a rubber-like material and is laterally held in the manner of a balloon that is part of a bladder catheter at the end portion of the guide part 7. The guide part 7 is insertable into the medullary space 2. The hollow body 12 is connected via the opening 7a to the end portion of the guide part 7. The wall thickness of the hollow body 12 is illustrated with exaggerated thickness in the Figures. The hollow body 12 adopts a basic position when the guide part 7 is relieved of pressure and, in this basic position, is situated substantially inside the cross-section of the guide part 7. The hollow body 12 can be inflated into an expanded position by the supply of pressure medium from the syringe 11. In this inflated position, it contacts the wall of the medullary space 2 and thus seals off the proximal section 2a of the medullary space 2 from the distal portion 2b of the medullary space 2. The guide part 7 can, as illustrated, be provided with a closure member 13 which on the one hand permits a reliable one-way (i.e. non-return) supply of the pressure medium introduced by the syringe 11 into the hollow body 12 and, on the other hand, is adjustable between a blocking position in which the removal of pressure medium is prevented and a release position in which the removal is allowed, it being advantageous to return the removed pressure medium back into the syringe 13.

The guide part 7 and the relief lines 8 and 9 can be combined into an interconnected handling unit as illustrated, or can be arranged separate from one another so that they can each be inserted and withdrawn separately. The relief lines 8 and 9 are constructed and arranged so that the end portion with the opening 8a of the one, first relief line 8 projects beyond the end portion of the guide part 7 connected to the hollow body 12 when in the operative position and thus forms an outward connection of the distal end portion 2b of the medullary space 2, whereas the end portion with the opening 9a of the second relief line 9 terminates prior to the end portion of the guide part 7 connected to the hollow body 12 as seen in the insertion direction and thus makes possible and an outward connection of the base region of the proximal portion 2a.

The guide part 7 and the relief lines 8 and 9 can also be formed differently, for example in the form of channels through the length of a common strip-shaped body, with one of these channels being connected to the hollow body 12.

Prior to insertion of the anchoring shaft 4 into the medullary space 2 prepared for its receipt, the guide part 7 and the relief lines 8 and 9 of the apparatus 6 are inserted into the medullary space 2 up to a predetermined depth necessary for the receipt of the anchoring shaft 4. The outer end of the guide part 7 can be fixedly connected to the syringe 11 or, as illustrated in FIG. 1, connected to the syringe 11 via a releasable coupling 14. In place of the closure member 13 illustrated, a different implementation can be provided, for example a closure arrangement integrated into the syringe 11 or the coupling 14.

To install the medullary space blocker 5, the syringe 11 filled with pressure medium is placed onto the guide part 7, whereupon the hollow body 12 is inflated by the supply of pressure medium into the guide part 7 from its base position situated in the region of the cross-section of the guide part 7 into the expanded position, thereby subdividing the medullary space 2. In the expanded position, the proximal portion 2a of the medullary space 2 is sealed off from the distal portion 2b. Bone cement is filled into the portion 2a of the medullary space by means of an outlet nozzle 15 which is insertable into the operation opening 3 up to a filling level F lying a predetermined dimension A below the operation opening 3. On filling with the bone cement, air and/or liquid situated in the base region of the portion 2a of the medullary space can make way for the bone cement and pass into the relief line 9 via the opening 9a positionable directly above the hollow body 12 and then be drawn off or sucked out of the relief line 9.

After filling the medullary space with bone cement and while the bone cement is still soft, the anchoring shaft 4 to be implanted is partially inserted into the bone cement with a greater portion projecting out of the operation opening 3 than is shown in the illustration. The free upper end region 16 of the portion 2a of the medullary space in the region of the distance A is then filled up by the displaced bone cement. Expelled air and/or liquid can be drawn off or, optionally, sucked, from the distal portion 2b of the medullary space 2 via the opening 8a of the relief line 8 situated underneath the hollow body 12. Correspondingly, a pressure increase in the distal portion 2b of the medullary space caused by air being expelled from the proximal portion 2a on the application of bone cement and/or on the insertion of the anchoring shaft 4 can also be prevented. The danger of formation of fat embolisms as a result of overpressure in the distal region of the medullary space is thus avoided.

After partial curing of the bone cement, the pressure medium can be drawn up into the cylinder of the syringe 11 after corresponding actuation of the closure member 13 and thus the hollow body 12 can be shrunk from its expanded position into the basic position situated in the cross-sectional region of the guide part 7. The hollow body 12 can then be withdrawn without causing any substantial distortion or other damage to the cement cylinder just formed. The relief lines 8 and 9 can be withdrawn from the medullary space 2 either together with the guide part 7 or separately from the guide part 7.

After the removal of the guide part 7 and the relief lines 8 and 9, the anchoring shaft 4 can be pressed in fully into the bone cement bed, which has not yet fully cured, into the position shown in FIG. 1. The channels in the cement cylinder formed through the guide part 7 and the relief lines 8 and 9 are then closed and filled up respectively by the expelled bone cement. Any remaining part of the bone cement expelled on complete insertion of the anchoring shaft 4 can be taken up in the upper end region 16 of the medullary space 2 since the degree of curing of the bone cement reduces from the deepest part of the portion 2a of the medullary space towards the upper end region 16 thereof.

The apparatus 6 described permits the placement of a temporarily insertable medullary space blocker 5 which can be simply positioned by inflation in a few seconds and, after curing of the bone cement, in an equally straightforward manner can be shrunk into the basic position, returned into the cross-sectional region of the guide part 7, and then removed from the medullary space. A substantial advantage of the medullary space blocker 5 described is that it can be matched to medullary spaces with different cross-sectional dimensions. Moreover, the dimensions of the medullary spaces do not have to be measured out. In particular, supplies of differently sized blocker elements or of special implantation tools do not have to be kept.

The apparatus 6 in accordance with FIGS. 5 and 6 substantially corresponds to that of FIGS. 1 to 4 but with the additional provision of a tubular displacement body 20 which is insertable into the medullary space 2 for sealing the applied bone cement. The displacement body 20 can, as illustrated, be formed by a hose part which is expansible transverse to the longitudinal direction of extension of the displacement body, which is closed at the end insertable into the medullary space 2, and which is connectable with its end protruding from the medullary space 20 to the syringe 11 or to a further source of pressure medium. Before or after inserting the anchoring shaft 4 into the medullary space 20, preferably after removal of the guide parts 7 and the relief lines 8 and 9 from the partially cured cement cylinder, the displacement body 20 can be inflated by the supply of pressure medium from the syringe 11a out of the basic position shown with the solid lines into an expanded position 20', illustrated with the dot-dashed lines, in order to seal the bone cement applied and to fill up the cavities left behind in the region of the guide part 7 and the relief lines 8 and 9. By returning the pressure medium into the syringe 11a, the displacement body 20 can be shrunk into the basic position in which it can be removed from the bone cement base. The cavity remaining in the region of the removed displacement body 20 can be filled up by the bone cement expelled on complete pressing in of the anchoring shaft 4 or with freshly supplied bone cement.

In the embodiment of FIGS. 7 and 8, the apparatus 6 further comprises an elastically deformable elongate sheath 22 which is guidable into the proximal portion 2b of the medullary space 2. The end of the elongate sheath 22 insertable into the medullary space 2 is closed off and the end lying outside the medullary space 2 is similarly connectable to a source of pressure medium, in the illustration to a corresponding syringe 11b. The sheath 22 is for temporarily lining the portion 2b of the medullary space prepared for the implantation. A tamponade for the proximal medullary space which is simple t o insert and remove can thus be achieved, in particular during the time of cement preparation, and can be used to staunch blood in place of a conventional tamponade formed with a gauze dressing. The sheath 22 can be inflated by the supply of pressure medium and pressed against the wall of the portion 2a of the medullary space as well as against the guide part 7 and the relief lines 8 and 9 and can be shrunk by the removal of pressure medium prior to the introduction of the bone cement and then withdrawn from the portion 2a of the medullary space. The sheath 22 can also be inserted into the medullary space 2 and inflated prior to the introduction of the apparatus 6 in order to seal off the medullary space 2 prior to installation of the medullary space blocker 5.

In accordance with the illustration of FIGS. 9 and 10, a dimensionally stable tube, for example of metal, can be provided as the guide part 7. The end portion of the tube, which is insertable into the medullary space 2 and which is closed in the axial direction, is surrounded by the hollow body 12 formed in this embodiment in the form of a ring 12a. The hollow body tightly closes around the guide part 7 when in the pressure-relieved base position. The hollow body can be inflated by the supply of pressure medium radially into its expanded position in which it extends around the end portion of the guide part 7 in the manner of a tire and closes off the portion 2a of the medullary space. The end portion of the guide part 7 projecting out of the medullary space 2 is closable via the coupling 14 and connectable via the coupling to the source of pressure medium. In this embodiment, the guide part 7 is centered within the medullary space 2 by the inflated hollow body 12 and can be used as a guide and centering element for the anchoring shaft 4 to be fitted into the medullary space 2.

The relief line 8 can be arranged separate from the guide part 7 or, as illustrated, formed in a telescopic arrangement by a tube passing substantially coaxially through the guide part 7. This tube is sealed off against the end portion of the guide part 7 surrounding the hollow body 12. The tube end having the opening 8a protrudes into the portion 2b of the medullary space. The anchoring shaft 4 is, as illustrated, formed with a bore 4a matched to the thickness of the guide part 7 and extending over the full length of the anchoring shaft 4. On implantation, the anchoring shaft 4 can be stuck onto the guide part 7. The guide part 7 is held inclined and can be positioned approximately in the false central axis of the medullary space 2. The anchoring shaft 4 can then be inserted into the portion 2a of the medullary space filled with bone cement.

After partial curing of the bone cement, the guide part 7 can be connected via the coupling 4 to the syringe 11. The pressure medium can then be returned into the cylinder of the syringe 11, thus shrinking the hollow body 12 into the basic position. The hollow body, together with the guide part 7 and the relief line 8, can then be withdrawn from the bore 4a of the anchoring shaft 4. The relief line 9 can then be withdrawn from the bone cement base in the manner described above. In this embodiment, the entire periphery of the wall of the expanded hollow body 12 is able to contact the wall of the medullary space 2 so that the formation of perforating openings along this wall is prevented. A secure seal between the medullary space portions 2a and 2b is thus achieved. Moreover, in this embodiment there are fewer cavities left behind along the wall of the proximal portion 2a after removal of the medullary space blocker 5 than in the previously described embodiments. As illustrated, there is in fact only the one channel formed by the relief line 9 which needs to be filled up by compression of the bone cement.

At least one of the relief lines 8 and 9 may also be formed by a dimensionally stable tube, for example of metal. In a related embodiment of the invention, which is not shown, the relief lines 8 and 9 may also be arranged telescopically. As shown in FIG. 11, the relief line 9 can be formed by a relief tube which is open in the base region of the portion 2a of the medullary space and which surrounds the guide part 7. Prior to the placement of the anchoring shaft 4 onto the guide part 7, this open relief tube can be removed from the bone cement base (which is cavity-free in the peripheral region), or, if the bore 4a has a correspondingly large cross-section, can be withdrawn together with the guide part 7 from the fitted anchoring shaft 4. An embodiment is also possible in which the arrangement of the relief lines 8, 9 or one of the relief lines 8, 9 is dispensed with. The apparatus of the invention is also suited for placement of medullary space blockers in other implantation regions, for example for knee prostheses or elbow prostheses.

In summary, the invention can be described as follows:

A tubular guide part 7 which is insertable into the medullary space 2 is connected to a source of pressure medium 11 and to a blocking element having the form of a hollow body 12 which can be inflated in the manner of a balloon. The hollow body 12 is inflated via the supply of pressure medium from a basic position situated in the cross-sectional region of the guide part 7 into an expanded position in which the hollow body seals off one portion 2a of the medullary space, which is to be filled with bone cement and is to receive a prosthesis shaft 4, from a neighboring portion 2b of the medullary space. After insertion of a part of the prosthesis shaft 4 into the bone cement bed, the hollow body 12 can be shrunk into its basic position by the removal of pressure medium and withdrawn from the medullary space 2 together with the guide part 7. The cavity in the bone cement bed ensuing therefrom is filled up by bone cement expelled during insertion of the remaining portion of the prosthesis shaft 4. In this manner, a medullary space blocker 5 is provided which can be temporarily installed in the medullary space 2 and then removed before the final curing of the bone cement.

What is claimed is:

1. A medullary space blocker for a medullary space of a tubular bone intended for receipt of an anchoring shaft of an endoprosthesis to be implanted with the use of bone cement, the medullary space blocker comprising a blocking element positionable at a predetermined depth in the medullary space, wherein the blocking element is implemented in the form of an elastically deformable hollow body which is expansible in the manner of a balloon and which is connected to a tubular guide part insertable into the medullary space and which is connectable via this guide part to a source of the pressure medium arranged outside the medullary space, wherein the hollow body is adjustable from a basic position situated substantially inside the cross-section of the guide part and which is adopted by the hollow body when the guide part is relieved of pressure, into an expanded position in which the cross-section of the medullary space is sealed off and which the hollow body adopts upon the supply of the pressure medium, wherein the hollow body can be returned to the basic position from the expanded position by the removal of the pressure medium, whereupon the hollow body can be removed from the medullary space with the guide part.

2. Apparatus for the placement of a medullary space blocker in the medullary space of a tubular bone intended for the receipt of an anchoring shaft of an endoprosthesis that is to be implanted with the use of bone cement, the medullary space blocker being in the form of an elastically deformable blocking element that is positionable in the medullary space for limiting a proximal portion of the medullary space that is intended for the receipt of the anchoring shaft and for the receipt of a bone cement bed surrounding the anchoring shaft, the apparatus comprising:

a tubular guide part that can be inserted into and withdrawn from the medullary space;

wherein a portion of the tubular guide part that is to be inserted into the medullary space is closed off in an axial direction and is connected to the elastically deformable blocking element;

wherein the blocking element has the form of a hollow body, which is expansible in the manner of a balloon;

wherein the tubular guide part is connectable outside of the medullary space to a source of a pressure medium; and, wherein the hollow body is adjustable between a basic position situated substantially inside the cross-section of the guide part and that the hollow body adopts when the guide part is relieved of pressure, and an expanded position in which the proximal portion of the medullary space to be filled with bone cement is sealed off from a distal portion of the medullary space and that the hollow body adopts upon the supply of a pressure medium.

3. Apparatus in accordance with claim 2, wherein the guide part is connected to a closure member that is adjustable between a blocking position which blocks the removal of the pressure medium and a release position which permits the removal of the pressure medium.

4. Apparatus in accordance with claim 2, wherein the guide part is associated with a tubular relief line which can be inserted into and withdrawn from the medullary space and which has an inlet aperture for air and/or liquid positionable in the insertion direction behind the portion of the guide part connected to the hollow body.

5. Apparatus in accordance with claim 4, wherein the guide part and at least one of the relief lines are combined to form a handling unit.

6. Apparatus in accordance with claim 4, wherein the guide part and at least one of the relief lines are arranged telescopically substantially coaxially to one another.

7. Apparatus in accordance with claim 2, wherein the guide part is associated with a second tubular relief line which can be inserted into and withdrawn from the medullary space and which has an inlet opening for air and/or liquid positionable in the insertion direction in front of the portion of the guide part connected to the hollow body.

8. Apparatus in accordance with claim 2, further comprising an elongate displacement body which can be inserted into the medullary space and which has the form of a hosing part which is expansible transverse to its elongate extension and which seals towards the hollow body and which is connectable to said source or a further source of a pressure medium and which can be inflated from a basic position into an expanded position by the supply of the pressure medium to compress the bone cement introduced into the medullary space.

9. Apparatus in accordance with claim 2, wherein the guide part is formed as a dimensionally stable centering element which can be inserted into the medullary space so as to be free standing and which is to be brought together with a throughhole passing through the anchoring shaft in the direction of its longitudinal axis, and wherein the hollow body is implemented in the form of a radially expansible ring surrounding the guide part.

10. Apparatus in accordance with claim 2, further comprising an elastically deformable sheath for temporarily lining the medullary space, wherein the sheath is insertable into the medullary space, seals against the hollow body and is connectable to said or a further source of a pressure medium, and can be pressed against the wall of the medullary space by means of the supply of the pressure medium.

* * * * *